(12) United States Patent
Yeh et al.

(10) Patent No.: US 9,579,403 B2
(45) Date of Patent: Feb. 28, 2017

(54) NANOSTRUCTURE, APPLIED DEVICE AND PREPARATION METHOD THEREOF

(71) Applicants: Chen-Sheng Yeh, Tainan (TW); Ming-Fong Tsai, Tainan (TW); Fong-Yu Cheng, Tainan (TW)

(72) Inventors: Chen-Sheng Yeh, Tainan (TW); Ming-Fong Tsai, Tainan (TW); Fong-Yu Cheng, Tainan (TW)

(73) Assignee: NATIONAL CHENG KUNG UNIVERSITY (TW)

( * ) Notice: Subject to any disclaimer, the term of this patent is extended or adjusted under 35 U.S.C. 154(b) by 643 days.

(21) Appl. No.: 13/947,360

(22) Filed: Jul. 22, 2013

(65) Prior Publication Data

US 2014/0241992 A1 Aug. 28, 2014

(30) Foreign Application Priority Data

Feb. 27, 2013 (TW) .............................. 102107108 A

(51) Int. Cl.
  *A61B 5/00* (2006.01)
  *A61K 49/00* (2006.01)
  *A61K 41/00* (2006.01)
  *B82Y 5/00* (2011.01)

(52) U.S. Cl.
  CPC ...... *A61K 49/0093* (2013.01); *A61K 41/0052* (2013.01); *B82Y 5/00* (2013.01)

(58) Field of Classification Search
  CPC ... A61B 5/0048; A61B 5/0062; A61B 5/0075; A61B 5/0059; A61B 5/0093; A61B 5/0095; A61K 9/51; A61K 9/5192
  USPC .......................... 424/489–495, 9.1, 9.32, 9.6
  See application file for complete search history.

(56) References Cited

U.S. PATENT DOCUMENTS

| 2010/0243020 A1* | 9/2010 | Norton ................... B82Y 20/00 136/244 |
| 2012/0014878 A1* | 1/2012 | Culha ................... C07H 21/00 424/9.1 |

OTHER PUBLICATIONS

Lim et al (Highly uniform and reproducible surface-enhanced Raman scattering from DNA-tailorable nanoparticles with 1nm interior gap, Nature Nanotechnology, vol. 6, Jul. 2011, pp. 452-460).*

Dong-Kwon Lim et al., "Highly uniform and reproducible surface-enhanced Raman scattering from DNA-tailorable nanoparticles with 1-nm interior gap", Nature Nanotechnology, vol. 6, No. 7 (2011), pp. 452-460.

* cited by examiner

*Primary Examiner* — Micah-Paul Young
(74) *Attorney, Agent, or Firm* — Volpe and Koenig, P.C.

(57) ABSTRACT

A nanostructure is described. The nanostructure includes a nanoparticle, a shell encompassing the nanoparticle, and a gap having a width ranging from 1.0 nm to 6.0 nm and located between the nanoparticle and the shell to enable the nanostructure to generate a fluorescence.

7 Claims, 3 Drawing Sheets

NANOSTRUCTURE, APPLIED DEVICE AND PREPARATION METHOD THEREOF

CROSS REFERENCE TO RELATED APPLICATION

This application claims benefit under 35 U.S.C. §119 of TW Application No. 102107108, filed Feb. 27, 2013, the contents of which is incorporated by reference as if fully set forth.

FIELD OF INVENTION

The present invention relates to a nanostructure, its applicable device and the preparation method for the nanostructure. The nanostructure of the present invention has the abilities of absorbing a near infrared ray, exhibiting a non-linear optical property and generating a two-photon fluorescence.

BACKGROUND

In recent years, nano-materials and nanotechnology have become the key point for research in every nation. A nanomaterial usually refers to a material with a size range from 1 nm to 100 nm. Since nanoparticles have a very small particle size and the number of atoms constituting the nanoparticle is far less than the typical particle, it thus has a great surface area and a high surface atomic ratio, and thereby the nanoparticle itself has a quantum effect. Therefore, nanoparticles have many specific properties and potential applications in the aspects of the catalyst, the electrode, the optical property and the mechanical property. Hence, nanomaterials and nanotechnology can be applied to various fields that have developmental potential.

Among the many metal materials for producing nanoparticles, gold was the earliest one to be investigated generally. Gold nanoparticles are considered as the best material for use in the living body due to its many advantages such as simple preparation method and high biocompatibility, such that biomedical research and development of gold nanoparticles has increased year by year.

The near infrared ray (NIR), especially between the region 1000~1350 nm, is known as the biological window in which the electromagnetic wave has better tissue penetration while not being absorbed by the skin tissue to achieve the detection and treatment for the deep tissues. Meanwhile, the biological tissue significantly reduces generation of auto-fluorescence when irradiated by the NIR. It goes without saying that a material that has the abilities of absorbing the NIR and generating the fluorescence can be applied in the biomedical field. However, an NIR-absorber with a size less than 100 nm is not available in that region, and so the application of the NIR-absorber in the living body is limited.

In view of the drawbacks of the prior art, the present invention describes a nanostructure which has a dominant component of gold having the ability of absorbing the NIR, and has the functions of combining the targeted drug, imaging and treatment. This nanostructure can serve as an imaging agent to combine with existing ultrasound and endoscope technology currently in development to become a novel diagnostic and treatment platform and to provide more applications. The summary of the present invention is below.

SUMMARY

In the nanostructure described in the present invention, a nanoparticle, a shell encapsulating the nanoparticle and a gap are included, wherein the gap has a width ranging from 1.0 nm to 6.0 nm and is located between the nanoparticle and the shell to enable the nanostructure to generate a fluorescence.

In another aspect, the present invention describes a near infrared ray absorption device including an input end and an output end, wherein the input end absorbs a near infrared ray having a wavelength between 1,000 nm and 1,350 nm and the output end releases the fluorescence.

In addition, the present invention also describes a method for preparing said nanostructure, including (a) providing a nanoparticle having a surface, (b) forming a metal layer on the surface of the nanoparticle, and (c) mixing the nanoparticle and the metal layer with an Au ion solution to form a core-shell structure for the nanostructure, wherein the Au ion solution has a volume being 0.8 to 2 fold that of the nanoparticle.

The nanostructure of the present invention represents a breakthrough in the limitations of the NIR wavelength and the particle size of the past, which has sufficient originality for revolutionary change in the existing non-optical imaging and therapeutic technology (i.e. endoscope and ultrasound) field. Because the nanostructure of the present invention has the abilities of absorbing the NIR and emitting the fluorescence, it can be applied to the biomedical field as well as the optical field. The present nanostructure can serve as an imaging agent and can be combined with ultrasound or endoscope devices to develop novel diagnostic and treatment platforms. In addition to solving the existing problems, the present nanostructure also provides additional applications to eliminate the limitations in the use of the infrared ray.

Other objects, advantages and efficacies of the present invention are described in detail below and taken from the preferred embodiments with reference to the accompanying drawings.

DETAILED DESCRIPTION OF THE PREFERRED EMBODIMENTS

Figure 1:
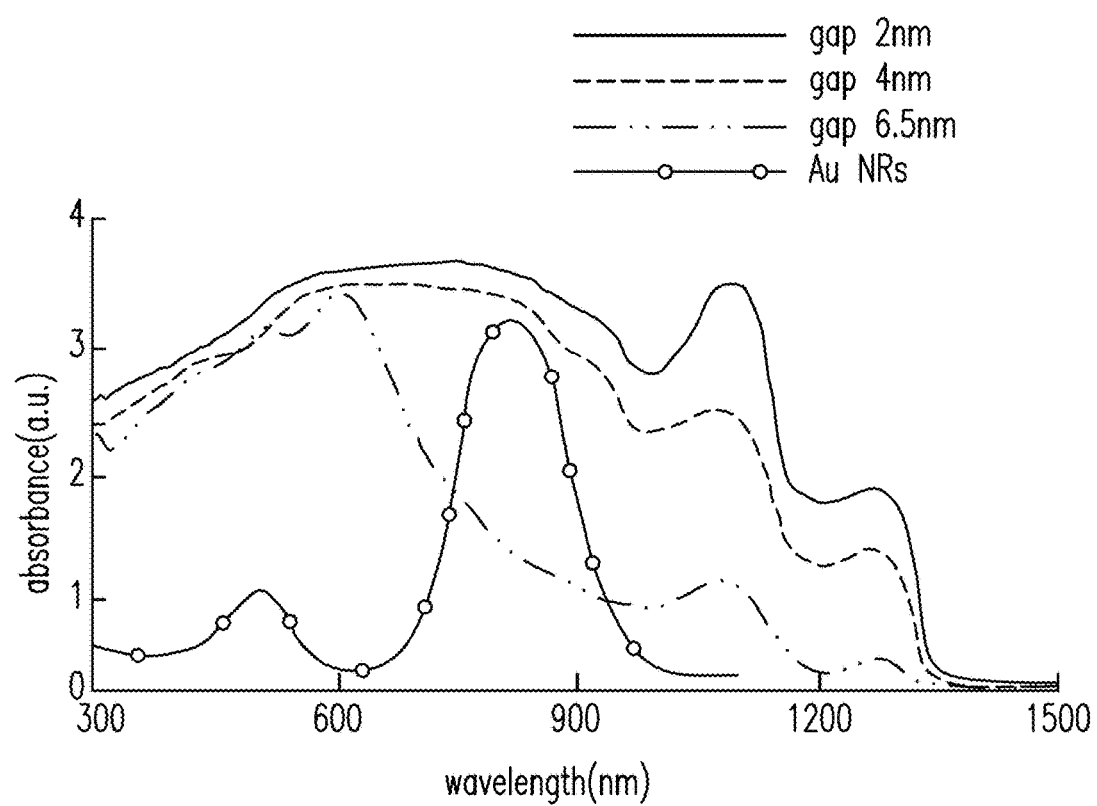
FIG. 1 is an absorbance spectra analysis of the nanostructures with different gaps prepared according to the preparation method of the present invention.

Further embodiments herein may be formed by supplementing an embodiment with one or more elements from any one or more of the other embodiments herein, and/or substituting one or more elements from one embodiment with one or more element from one or more of the other embodiments herein.

EXAMPLES

The following non-limiting examples are provided to describe particular embodiments. The embodiments throughout may be supplemented with one or more details from one or more examples below, and/or one or more elements from an embodiment may be substituted with one or more details from one or more of the examples below.

The present invention provides a nanostructure having a basic core-shell structure, wherein the core is a nanoparticle, and there is a gap having a width ranging from 1.0 nm to 6.0 nm between the nanoparticle and the shell, such that the nanostructure has the ability of generating the fluorescence. The luminescence ability of the nanostructure is due to its ability to absorb NIR (in particular, the 1000~1350 nm NIR), such that the NIR hyperthermia generates the non-linear optical property and the two-photon fluorescence by absorbing the thermal energy of the NIR.

The difference between the present nanostructure and the common nanoparticle resides in the gap between the core and the shell, the size of which can be regulated by the preparation method provided in the present invention. In the nanostructure prepared by the preparation method of the present invention, the gap having a width ranging between 1.0 nm and 6.0 nm demonstrates good absorbability to the NIR in the 1000 to 1350 nm wavelength, and this ability can not be achieved by the common nanostructure.

It can be observed through the use of a transmission electron microscope (TEM) that the nanostructure of the present invention has a core-shell structure. The TEM image shows that the nanostructure of the present invention has a length of about 53.2 nm, a width of about 22.1 nm, a gap between the core and shell of about 2.0 nm and a shell having a thickness of about 6.2 nm.

According to one embodiment of the present invention, the core of the nanostructure is a gold (Au) nanoparticle. Since Au has high biocompatibility, the Au nanoparticle is considered as a material most applicable for use in a living body. Accordingly, the nanostructure of the present invention having a dominant material of Au can be generally applied to various medical platforms such as ultrasound, endoscopy and computer tomography, or be combined with other agents (e.g., photosensitizer) to serve as a non-linear optical imaging contrast tool and a photodynamic therapeutic agent, and thus integrate diagnostic and therapeutic applications.

The material of the shell of the present invention is selected from one of gold (Au), silver (Ag), platinum (Pt), palladium (Pd), nickel (Ni) and an alloy thereof. In one embodiment of the present invention, the material of the core is Au while that of the shell is Ag. In another embodiment of the present invention, the material of the core is Au while that of the shell is an Au—Ag alloy.

Since the present nanostructure has the abilities of absorbing the NIR, exhibiting a non-linear optical property and generating a two-photon fluorescence, it can be utilized as an energy transfer device (in particular the NIR absorbing device) where its input end can absorb the NIR having a wavelength between 1000 nm and 1350 nm and its output end releases the fluorescence. Actually, the NIR absorbing device is a nanostructure with a size smaller than 100 nm, and thus it can be applied to a living body such as a mammal so that the process of the energy transfer as described above occurs in the body and facilitates the image analysis and drug delivery.

In order to prepare the above nanostructure, the present invention provides a preparation method including (a) providing a nanoparticle having a surface, (b) forming a metal layer on the surface of the nanoparticle, and (c) mixing the nanoparticle and the metal layer with an Au ion solution to form a core-shell structure for the nanostructure, wherein the Au ion solution has a volume being 0.8 to 2 fold that of the nanoparticle.

According to the present invention, the nanoparticle includes but is not limited to a nanotube, a nanorod and a nanowire. In the preferred embodiment of the present invention, the nanoparticle is an Au nanorod. The material of the metal layer is one selected from Au, Ag, Pt, Pd, Ni and an alloy thereof. In the above step (c), the Au ion solution is added in order to regulate the gap between the core and the shell. The Au ion solution used in the embodiment of the present invention is chloroauric acid (HAuCl4) which has a volume being 0.8 to 2 fold that of the nanoparticle, preferably 0.8 to 1.5 fold.

The embodiments for preparing the nanostructure of the present invention are described in detail below.

Preparation of Au Nanorods

In each of two 50 ml centrifuge tubes, 1.822 g of cetyltrimethylammonium boride (CTAB) and 5.4 ml of 5 mM chloroauric acid (HAuCl4.3H2O) are uniformly mixed with water to prepare a solution having a volume of 50 ml. When the CTAB is completely dissolved, the solution becomes an orange, clear solution.

The two tubes of 50 mL CTAB mixed solution are poured into a flask and stirred, and then 60 μL of 0.1M silver nitrate (AgNO3) is added to the flask. After uniformly mixing the solution, 600 μL of 0.1M ascorbic acid is added to the flask within 5 minutes, which creates a colorless transparent solution. Following the addition of the ascorbic acid, 40 μL of 10 mM sodium borohydride (NaBH4) is added within 5 seconds to react for 2 hours, which creates a reddish brown solution. The resulting product is collected in a centrifuge at 10,000 rpm for 20 minutes to remove the supernatant, the precipitate is washed with ultrapure water and centrifuged again at 10,000 rpm for 20 minutes to remove the supernatant and to collect the precipitate in the tube. Finally, the precipitate is redispersed in ultrapure water, and the macro molecules are centralized at the lower layer of the tube at 2,000 rpm for 30 minutes. The upper layer is removed and put into a new tube.

Synthesis of Au/Ag Core-Shell Nanorods

500 μL of 100 ppm Au nanorod solution and 500 μL of 100 mM CTAB are mixed to form 1 mL of a mixture containing 50 mM CTAB and 50 ppm Au nanorods. 5 mL of 1 wt % poly(vinylpyrrolidone) (PVP) is poured into a vial, and 1 mL of the mixture containing 50 mM CTAB and 50 ppm Au nanorods is added to the vial.

950 μL of 1 mM AgNO3 solution and 125 μL of 100 mM ascorbic acid solution are added into the vial and uniformly mixed through stirring. 0.25 mL of 100 mM sodium hydroxide solution is then added to the mixture to react with the mixture for 10 minutes. When the color of the solution changes, it means that the Ag nano layer has formed on the Au nanorod, and the final color of this solution is citrus red. The product is collected by using a centrifuge at 10,000 rpm for 10 minutes to remove the supernatant, and the precipitate is washed with deionized water. The precipitate is centrifuged at 10,000 rpm for 10 minutes again to remove the supernatant, and the precipitate is redispersed with deionized water to become a 1 mL solution. The end product is the Au/Ag core-shell nanorod which is covered with an Ag nanolayer.

As shown in FIG. 1, the size of the gap can be controlled through different experimental conditions (i.e. by changing the volume of the Au ion solution). The size of the gap will affect the intensity of the NIR absorbance. The methods for preparing nanoparticles with different sizes of the gap are as follows.

Syntheses of the Nanostructure of Au Nanorod in Au/Ag Alloy Shell with 2 nm and 6.5 nm Gaps The nanostructure of Au nanorod in Au/Ag alloy shell with 2 nm gap 1 mL Au/Ag core-shell nanorod solution, 500 μL of 100 mM CTAB solution, 125 μL of 100 mM ascorbic acid and 700 μL of 1 mM Au ion solution are in turn added to 5375 μL of deionized water at room temperature and stirred for 15 minutes. The solution is the nanostructure of Au nanorod in Au/Ag alloy shell with a 2 nm gap and should be calp.

The Nanostructure of Au Nanorod in Au/Ag Alloy Shell with 6.5 nm Gap 1 mL Au/Ag core-shell nanorod solution, 500 μL of 100 mM CTAB solution, 125 μL of 100 mM ascorbic acid and 400 μL of 1 mM Au ion solution are in turn added to 5375 μL of deionized water at room temperature and stirred for 15 minutes. The solution is the nanostructure of Au nanorod in Au/Ag alloy shell with a 6.5 nm gap and should be hyacinthine.

The products of the above reactions are centrifuged at 10,000 rpm for 10 minutes. After the supernatant is removed, the products are washed with saturated brine and centrifuged again at 10,000 rpm for 10 minutes to remove the supernatant. The resulting precipitates are washed with deionized water and centrifuged at 10,000 rpm for 10 minutes. The final products are redispersed in deionized water to form a 1 mL solution.

Based on the above disclosures, it can be known that the core-shell nanostructure changes from the Au/Ag core-shell nanostructure to the Au nanorod in Au/Ag alloy shell nanostructure after the gap is generated. This means that the gap is generated inside the original Au nanorod to create the Au/Ag alloy shell.

As shown in FIG. 1, the Au nanorod in Au/Ag alloy shell nanostructure with different gap sizes can be controlled by changing the volume of the Au ion solution. According to the above preparation methods, the Au nanorod in Au/Ag alloy shell nanostructures with 2 nm, 4 nm and 6.5 nm gaps are prepared and their absorbance to NIR with different wavelengths are measured. The measurements show that the nanostructures with 2 nm and 4 nm gaps have better absorbance while the nanostructure with 6.5 nm gap has weaker absorbance to NIR higher than the 600 nm wavelength. In order to prepare a nanostructure having good absorbance to NIR at wavelengths ranging between 1,000 and 1,350 nm, the width of the gap is preferably set between 1.0 nm and 6.0 nm.

According to the embodiment of the present invention, the nanostructures with 2 nm and 6.5 nm gaps are obtained by adding 700 μL and 400 μL of the 1 mM Au ion solution into the solution containing the Au/Ag core-shell nanorods. Because the starting material for preparing the Au nanorod-Au/Ag alloy shell nanostructure is 500 μL of Au nanorod solution containing 100 ppm Au, it is estimated therefrom that the volume of the Au ion solution is about 0.8 to 2 fold that of the nanoparticle, preferably 0.8 to 1.5 fold, so as to generate nanostructures with better NIR absorbance.

The various specific solutions used in the above preparations such as the CTAB, the HAuCl4, and the AgNO3 solutions, are only exemplary embodiments which do not limit the scope of the present invention. For example, the CTAB used in the above embodiments is cetyltrimethylammonium boride, but the skilled person in the art should realize that the surfactants with different chain lengths (i.e. the surfactant with 4 to 18 carbon chains) may be used to prepare the nanostructures in the present invention.

The ex vivo Test of the Present Nanostructures

The present nanostructures prepared by the above preparation methods are mixed with A549 cancer cells. The A549 cells are pre-treated with a solution containing $8.7 \times 10^{10}$ particle/mL Au nanorod-Au/Ag alloy shell nanostructure or a solution containing Au nanorod-Au/Ag alloy shell nanostructure modified with toluidine blue O (TBO). Then, the cells are irradiated with a 1230 nm laser ($6.5 \times 10^6$ W/cm2), and the cell viability is observed at different points in time. The result of mixing the Au nanorod-Au/Ag alloy shell nanostructure with the cells shows that the cells are not damaged and maintain the same morphology over time. However, the result of mixing the Au nanorod-Au/Ag alloy shell nanostructure modified with TBO with the cells shows that the cells begin to die and cell atrophy is generated over time.

After the Au nanorod-Au/Ag alloy shell nanostructure modified with TBO is injected into the vessel of the a mouse's ear, an in vivo test is performed by irradiating the ear with a 1230 nm laser, and the images of the mouse's ear are observed by a fluorescence microscope. Based on the two-photo fluorescence image, the third-harmonic generation image and the second-harmonic generation image observed by the fluorescence microscope, it can be seen that the Au nanorod-Au/Ag alloy shell nanostructure modified with TBO penetrates the vessel into the surrounding tissues and remains when it is injected into the mouse's ear. The fluorescence of the material can be detected when an external light source irradiates the mouse, which indicates that the material has the function of imaging detection in vivo.

Based on the above results, it is known that the present nanostructure not only facilitates the death of the cancer cells via the laser irradiation in the ex vivo study, but also inhibits the growth of the tumor via the laser irradiation in the in vivo study. Therefore, the present nanostructure has the potential to be developed as a therapeutic tool for cancer in mammals. The multi-functional nanomaterial provided in the present invention can be combined with ultrasound, a mature clinical procedure, and the developing non-linear optical endoscope, while it also has the potential to become a computer chromatography agent.

The nanostructure can be combined with a photosensitizer to serve as a non-linear optical image contrast tool and an agent for the photodynamic therapy.

The Au nanorod-Au/Ag alloy shell nanostructure where the surface is modified with a photosensitizer, TBO 1 mL of Au nanorod-Au/Ag alloy shell nanostructure is placed into a glass bottle and 67 μL of 7.5 mM 3-mercaptopropionic acid (MPA) is added thereto and incubated in a sonicator for 2 hrs. Subsequently, the mixture is incubated at room temperature overnight and then centrifuged at 10,000 rpm for 10 minutes. The supernatant is removed, and the precipitate is washed with deionized water and centrifuged at the same speed for 10 minutes again. The resulting supernatant is removed, and the precipitate is re-dispersed in a phosphate buffer solution (PBS) (pH 5.5) to form 1 mL solution and placed in a glass sample bottle. Then, 50 μL of 10 mM crosslinker (EDC/NHS) is added to the bottle and the bottle is incubated in the sonicator for 30 minutes. 130 μL of 30 μM TBO is added into the bottle to resume the sonication for 6 hrs, and the mixture is centrifuged at 10,000 rpm for 10 minutes to remove the supernatant. The precipitate is washed with deionized water and this step is repeated twice, and the final product is re-dispersed in the PBS buffer solution (pH5.5) to form 1 mL solution.

Modifying with the PEG Molecular on the Surface of the Au Nanorod-Au/Ag Alloy Shell Nanostructure Modified with a Photosensitizer TBO The product resulting from the above steps is placed in a glass sample bottle, 50 μL of 10 mM crosslinker EDC/NHS is added to the bottle and the bottle is placed in a sonicator for 30 minutes. 100 μL of 10 μM PEG is added to the bottle, the sonication is resumed for 6 hrs, and the mixture is centrifuged at 10,000 rpm for 10 minutes to remove the supernatant. Then, the precipitate is washed with deionized water and this step is repeated twice, and the final product is re-dispersed in deionized water to form 1 mL solution.

Figure 2:
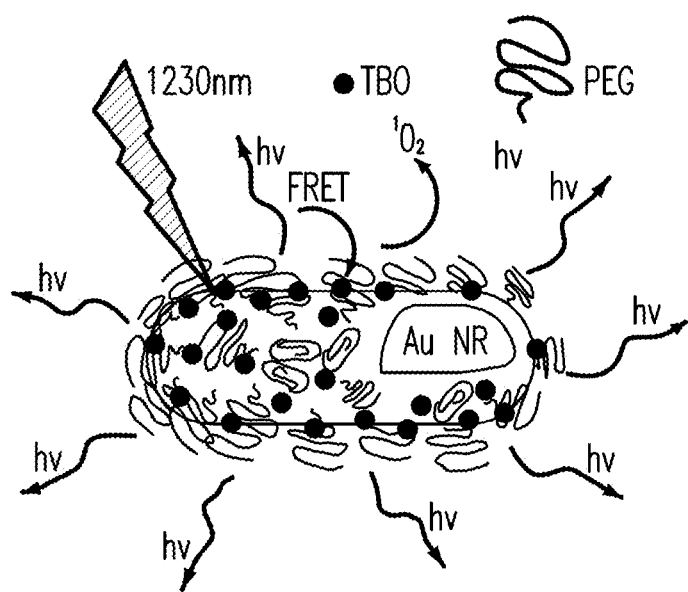
FIG. 2 is a diagram showing the process by which the nanostructure of the present invention combines with the photosensitizer to serve as a non-linear optical imaging contrast or a photodynamic therapeutic agent.

FIG. 2 is a diagram showing the process by which the nanostructure of the present invention combines with the photosensitizer to serve as a non-lineal optical imaging contrast or a photodynamic therapeutic agent. As shown in FIG. 2, the nanostructure of the present invention has a core being an Au nanorod (Au NR) and a shell. The nanostructure is modified with a photosensitizer TBO on the surface thereof and then modified with the PEG according to the above-mentioned preparations, such that it may be used as an image contrast and a photodynamic therapeutic agent. Since the present nanostructure absorbs the NIR at 1,000-1,350 nm, it will emit the two-photon fluorescence (615 nm) under the irradiation of the NIR (e.g., at 1230 nm). This 615 nm fluorescence will be absorbed by the TBO to generate singlet oxygen that is toxic to the cancer cells. The process in which the fluorescence generated by the nanostructure is absorbed by the TBO thereon is referred as fluorescence resonance energy transfer (FRET). The nanostructure not only provides the function of image analysis but also causes the toxic effect to the cancer cells because it can release the fluorescence and the singlet oxygen (1O2).

An Example of Photothermal Therapy

Figure 3:
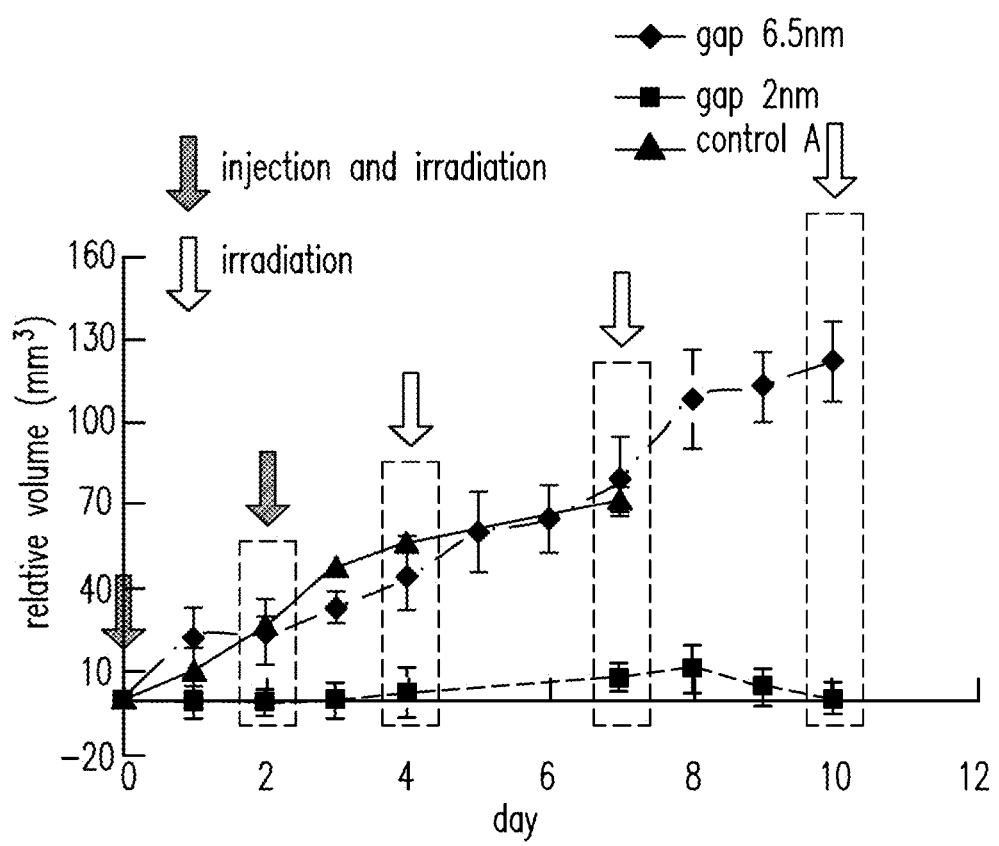
FIG. 3 is a diagram showing the results of combining the nanostructure of the present invention with the photothermal therapy to treat tumors in mice.

FIG. 3 is a diagram showing the results of the present invention with the photothermal to treat tumors in mice. The photothermal therapeutic test is performed where the Au nanorod-Au/Ag alloy shell nanostructure with the 2 nm gap (that absorb the NIR) and the 6.5 nm gap (that does not absorb the NIR) are compared with a control group. As shown in FIG. 3, these materials were injected into the tumors of the mice, and the mice were irradiated by a 1,024 nm laser for 7 minutes on days 0, 2, 4, 7 and 10. In the control group where the mice were not injected with the Au nanorod-Au/Ag alloy shell nanostructure, the tumor size increased over time, which indicates that the laser irradiation alone cannot provide the therapeutic effect. In the experimental group where the mice were injected with the Au nanorod-Au/Ag alloy shell nanostructure having the 6.5 nm gap, the tumor size also increased over time because the Au nanorod-Au/Ag alloy shell nanostructure having the 6.5 nm gap cannot absorb the NIR and thus does not cause any therapeutic effect, although the mice were injected with the material and irradiated. In the experimental group where the mice were injected with the Au nanorod-Au/Ag alloy shell nanostructure having the 2 nm gap, the tumor size decreased over time and even almost disappeared. This is because the Au nanorod-Au/Ag alloy shell nanostructure having the 2 nm gap absorbs the NIR and generates hyperthermia so as to kill the cancer cells, and therefore the therapeutic effect is increasingly effective over time.

In another medical application, the present nanostructure has the non-linear optical property so as to develop as a novel endoscope diagnostic and therapeutic technique when combined with an endoscope. The present nanostructure may deliver the drug via the endoscope and break through the limitation of using a near infrared light source in the past, in additional to providing images. In addition, the present nanostructure can also be combined with ultrasound therapeutic techniques to provide a structural analysis function that breaks through the limitation of traditional ultrasound, which detects only the shape or dissection. It can be seen that the applications of the present nanostructure are widespread and can be multiplied so as to generate a revolutionary change in existing non-optical imaging and therapeutic techniques.

EMBODIMENTS

1. A nanostructure, comprising:
    a nanoparticle;
    a shell encapsulating the nanoparticle; and
    a gap having a width ranging from 1.0 nm to 6.0 nm, and located between the nanoparticle and the shell to enable the nanostructure to generate a fluorescence.

2. A nanostructure as claimed in Embodiment 1, wherein the nanostructure further comprises abilities of absorbing a near infrared ray, exhibiting a non-linear optical property and generating a two-photon fluorescence.

3. A nanostructure as claimed in the preceding Embodiments, wherein the nanostructure has a size smaller than 100 nm.

4. A nanostructure as claimed in the preceding Embodiments, wherein the material of the nanoparticle includes gold.

5. A nanostructure as claimed in the preceding Embodiments, wherein the shell includes one being selected from a group consisting of a gold, a silver, a platinum, a palladium, a nickel and an alloy thereof.

6. A nanostructure as claimed in the preceding Embodiments, wherein the nanostructure is further configured to be combined with an imaging device to carry out an image analysis and a drug delivery for a mammal.

7. A nanostructure as claimed in the preceding Embodiments, wherein the imaging device is one selected from a group consisting of a photosensitizer, an endoscope, an ultrasound and a computer tomography.

8. A near infrared ray absorption device, comprising:
    an input end absorbing a near infrared ray having a wavelength between 1,000 nm and 1,350 nm; and an output end releasing a fluorescence.

9. A near infrared ray absorption device as claimed in the preceding Embodiments, wherein the near infrared ray absorption device has a size smaller than 100 nm.

10. A method for preparing a nanostructure, comprising steps of:
    (a) providing a nanoparticle having a surface;
    (b) forming a metal layer on the surface of the nanoparticle; and
    (c) mixing the nanoparticle and the metal layer with an Au ion solution to form a core-shell structure for the nanostructure, wherein the Au ion solution has a volume being 0.8 to 2 fold that of the nanoparticle.

11. A method as claimed in the preceding Embodiments, wherein step (c) further comprises adding an ascorbic acid solution.

12. A method as claimed in the preceding Embodiments, wherein the Au ion solution is a choloroauric acid which has a volume of 0.8 to 1.5 fold that of the nanoparticle.

13. A method as claimed in the preceding Embodiments, wherein the core-shell structure comprises a gap having a width ranging from 1.0 nm to 6.0 nm.

14. A method as claimed in the preceding Embodiments, wherein the core-shell structure has a shell with a thickness, further comprising:
(d) adjusting the thickness of the shell of the core-shell structure while maintaining the width of the gap.

15. A method as claimed in the preceding Embodiments, wherein the thickness ranges from 2 nm to 7 nm.

It is understood, that this invention is not limited to the particular embodiments disclosed, but is intended to cover all modifications which are within the spirit and scope of the invention as defined by the appended claims, the above description, and/or shown in the attached drawings.

What is claimed is:

1. A nanostructure, comprising:
a nanoparticle;
a shell encapsulating the nanoparticle; and
a gap having a width ranging from 1.0 nm to 6.0 nm, and located between the nanoparticle and the shell to enable the nanostructure to generate a fluorescence and absorb a near infrared ray having a wavelength between 1,000 nm and 1,350 nm.

2. A nanostructure as claimed in claim 1, wherein the nanostructure further comprises abilities of exhibiting a non-linear optical property and generating a two-photon fluorescence.

3. A nanostructure as claimed in claim 1, wherein the nanostructure has a size smaller than 100 nm.

4. A nanostructure as claimed in claim 1, wherein the material of the nanoparticle includes gold.

5. A nanostructure as claimed in claim 1, wherein the shell includes one being selected from a group consisting of a gold, a silver, a platinum, a palladium, a nickel and an alloy thereof.

6. A nanostructure as claimed in claim 1, wherein the nanostructure is further configured to be combined with an imaging device to carry out an image analysis and a drug delivery for a mammal.

7. A nanostructure as claimed in claim 6, wherein the imaging device is one selected from a group consisting of a photosensitizer, an endoscope, an ultrasound and a computer tomography.

* * * * *